United States Patent [19]

Horwath

[11] Patent Number: 4,593,001

[45] Date of Patent: Jun. 3, 1986

[54] HIGH TEMPERATURE ISOMERIZATION PROCESS

[75] Inventor: Robert O. Horwath, Westport, Conn.

[73] Assignee: Nabisco Brands, Inc., East Hanover, N.J.

[21] Appl. No.: 569,377

[22] Filed: Jan. 9, 1984

[51] Int. Cl.⁴ .................. C12P 19/24; C12N 9/92; C12R 1/06
[52] U.S. Cl. ................................. 435/94; 435/234; 435/830
[58] Field of Search .................. 435/94, 234, 830

[56] References Cited

U.S. PATENT DOCUMENTS

| | | | |
|---|---|---|---|
| 3,645,848 | 2/1972 | Lee et al. | 435/94 |
| 3,817,832 | 6/1974 | Lloyd et al. | 435/94 |
| 4,059,489 | 11/1977 | Meers | 435/830 X |
| 4,410,627 | 10/1983 | Lloyd et al. | 435/94 |
| 4,411,996 | 10/1983 | Lloyd | 435/94 |

Primary Examiner—Lionel M. Shapiro
Attorney, Agent, or Firm—Richard Kornutik

[57] ABSTRACT

The invention relates to a method for producing a glucose isomerizing enzyme which is functional at temperatures over 90°, utilizing a strain microorganisms having the identifying characteristics of Arthrobacter sp. ATCC 21748.

3 Claims, No Drawings

HIGH TEMPERATURE ISOMERIZATION PROCESS

FIELD OF THE INVENTION

This invention relates to a process for converting glucose to fructose. More specifically, it relates to the use of a glucose isomerase derived from a microorganism to convert glucose to fructose at high temperatures.

BACKGROUND OF THE INVENTION

The sugar fructose is one of the sweetest sugars known. It has long been known in the art to produce fructose by the isomerization of the relatively less sweet, and less expensive sugar, glucose, utilizing an enzyme having glucose isomerase activity. Extensive descriptions of the process of enzymatic conversion of glucose to fructose may be found in Hamilton, et al. "Glucose Isomerase a Case Study of Enzyme-Catalysed Process Technology", *Immobilized Enzymes in Food and Microbial Processes,* Olson et al., Plenum Press, N.Y., (1974), pp. 94–106, 112, 115–137; Antrim, et al.; "Glucose Isomerase Production of High-Fructose Syrups", *Applied Biochemistry and Bioengineering,* Vol. 2, Academic Press (1979); Chen, et al., "Glucose Isomerase (a Review)", *Process Biochem.,* (1980), pp. 36–41; Nordahl, et al. "Fructose Manufacture from Glucose by Immobilized Glucose Isomerase", *Chem. Abstracts,* Vol. 82, (1975), Abs. No. 110316h; and Takasaki, "Fructose Production Glucose Isomerase", *Chem. Abstracts,* Vol. 82, (1975), Abs. No. 110316h; and Takasaki, "Fructose Production by Glucose Isomerase", *Chem. Abstracts,* Vol. 81, (1974), Abs. No. 7647a.

The amount of fructose which may be obtained from the isomerization reaction of glucose is dependent upon the equilibrium of the reaction. Fructose yields can be substantially improved when the reaction is conducted at temperatures above 50° C., and preferably over 60° C. Unfortunately, the higher temperatures necessary to increase isomerization rate have, in the past, also had the adverse effect of denaturing the glucose isomerase, thus reducing the activity and stability of the enzyme. Therefore, for the use of a glucose isomerase to convert glucose to fructose to be exploited to its full potential, a type of enzyme with high resisitance to thermal denaturation is necessary.

The search for high-yield, thermostable glucose isomerase has been progressing for many years. Among the most common sources of glucose isomerase (also frequently referred to as xylose isomerase, because of the ability to convert xylose to xylulose) are a wide range of microorganisms. Among the organisms which have been demonstrated to be glucose isomerase producers are: *Streptomyces flavovirens, Streptomyces achromogenes, Streptomyces echinatus, Streptomyces albus, Streptomyces wedmorensis, Streptomyces phaeochromogenes, Streptomyces bobiliae, Streptomyces olivochromogenes, Streptomyces venezuelae, Aerobacter aerogenes, Aerobacter cloacae, Bacillus coagulans, Bacillus megaterium, Bacillus fructosus, Brevibacterium pentaaminoacidicum, Escherichia intermedia, Leuconostoc mesenteriodes,* and *Paracolobactrum aerogenoides,* and various species of the genera Nocardia, Micromonospora, Microbispora, Microellobospora and Arthrobacter. The thrust of reasearch in this area has been identification of a strain of glucose isomerase producing microorganism which synthesizes a thermally stable enzyme. Among the better known and more successful organisms useful in this respect are *Bacillus stearothermophilus* (U.S. Pat. No. 3,826,714), Ampulariella sp (U.S. Pat. No. 4,308,349); Streptomyces sp. (U.S. Pat. No. 4,317,883) and *Psuedonocardia thermophila* (Japanese Pat. No. SHO 49[1974] 30588). Of particular interest to the present invention, however, are members of the genus Arthrobacter.

The use of the genus Arthrobacter for the production of glucose isomerase is well known. U.S. Pat. No. 3,935,068 describes a cell-free enzyme system which is aggregated by the use of flocculation and which is capable of continuous isomerization, Arthrobacter is used as a source of the enzyme to be flocculated, within a temperature range of 50°–90° C. U.S. Pat. No. 3,817,832 relates to a method of isomerizing glucose wherein a glucose solution is passed through a bed of microbial cells in which the glucose isomerase has been fixed or stabilized, within a temperature range of 20° to 80° C. and at a pH between 6 and 9. Arthrobacter is the primary microorganism contemplated in this invention. U.S. Pat. No. 4,304,857 relates to a method of whole cell immobilization whereby wet, glucose isomerase-containing microorganisms, preferably Arthrobacter, are added to fumed silica, the resulting mixture extruded, and the cells dried. The resulting particles may be used for, among other enzymatic transformation reactions, the isomerization of glucose to fructose. U.S. Pat. No. 4,059,489 discloses a process for the continuous production of glucose isomerase by maintenance of a limiting amount of nutrient in the cell culture medium, and the use of the enzyme so produced to isomerase glucose to fructose, at a temperature within the range of 20°–90° C. Arthrobacter is among the preferred organisms for this process.

U.S. Pat. No. 3,645,848 (Reissue Nos. 29,689–29,692) relates to a process of utilizing Arthrobacter for the production of glucose isomerase which is operable at temperature of up to 90° C., at a preferred pH of 8. U.S. Pat. No. 3,821,086 (Reissue Nos. 29,130 and 29,136) discloses an enzymatic process utilizing immobilized microbial cells, the preferred example of which is Arthrobacter.

As noted previously, the desired yields are significantly increased at high temperatures by shifting the equilibrium of the isomerization reaction in favor of fructose, and a glucose isomerase which retains its activity, at very high temperatures is highly desirable. It has now been found that a strain of Arthrobacter, ATCC 21748, produces an enzyme which retains its capacity for isomerization at temperatures over 90° C., a significant improvement over previously known Arthrobacter strains.

BRIEF DESCRIPTION OF THE INVENTION

The present invention relates to a method for isomerizing glucose to fructose comprising contacting a glucose containing solution, under isomerization conditions, at a temperature between about 90° C. to about 110° C. with a glucose isomerizing enzyme obtained from a biologically pure culture of a strain of microorganism having the identifying characteristics of Arthrobacter sp ATCC 21748.

DETAILED DESCRIPTION OF THE INVENTION

The present invention provides a thermostable glucose (xylose) isomerase which is useful in the high-temperature conversion of glucose to fructose. Unlike other Arthrobacter strains, the preferred strain, Arthrobacter sp ATCC 21748, of the present invention produces an enzyme which is significantly active at temperatures over 90° C.; the enzyme produced by said strain also retains a higher percentage of yield at increased temperatures than many other well-known thermophilic glucose isomerase producers. This strain is presently publicly available from the American Type Culture Collection, 12301 Parklawn Drive Rockville, Md. 20852-1776 under the accession number ATCC 21748.

The organisms of the preferred strain of the invention may be grown on a variety of different media, such as corn steep water medium, corn-steep water-glucose medium, yeast wash-water or yeast extract medium. It has been found, however, that the nutrient medium must contain xylose as an inducer of the enzyme. Additionally, the inclusion of magnesium in the medium appears to promote growth. The optimal temperature for the growth of the organism and the production of the enzyme appears to be between 30°-32° C., with a preferred pH between 6.5-7.8. Yields of the enzyme under these conditions generally range from about 10 to 30 glucose isomerase units (GIU)/ml.

The enzyme so produced is operable at a wide range of temperatures. However, its primary advantage lies in the fact that it is capable of functioning, with a relatively small loss of activity, at temperatures of over 90° C. Conditions under which isomerization may be carried out vary, but the best results are achieved when the glucose containing solution has a concentration of glucose in the range of 5 to 40% by weight and preferably in the range of from about 15 to 20%. The pH of the glucose containing solution should be maintained within the range of 5.5 to 8. However, it was unexpectedly discovered that the preferred pH will depend upon the temperature at which the reaction is conducted: at 60° C., the optimum pH is 7.5-7.8; at 90° C., the pH should be within the range of 6.5-7, and most preferably is maintained at 6.8. Maintenance of the pH within this range during the isomerization reaction is important, because outside this range the isomerase will be rapidly inactivated, and significant amounts of unwanted by-products, such as color bodies or psicose, may be produced. However, it will be noted that the pH range and the preferred pH of the reaction conditions utilizing Arthrobacter sp ATCC 21748 is lower than any described previously. In the glucose-containing solution may also be included various ion activators and/or stabilizers such as magnesium or cobalt.

Yields of fructose will, of course, vary according to the temperature at which the isomerization reaction is run. However, it should be noted that enzyme preparation of the present invention shows a higher percentage of retained yield with an increase of temperature from 80° C. to 95° C. than a wide variety of other known microorganisms (see Table 1).

The process of the present invention may be better understood with reference to the following Examples, which are not intended to be limiting to the scope of the invention.

EXAMPLE 1

This example describes a method of culturing the glucose-isomerase producing Arthrobacter sp. ATCC 21748.

The nutrient medium for the culturing of Arthrobacter sp 21748 may be prepared as follows: (all % weight/l volume):

| | |
|---|---|
| Xylose | 1% |
| Corn steep liquor | 2% |
| $MgSO_4.7H_2O$ | 0.1% |
| $CoCl_2.6H_2O$ | 0.025% |
| Agar | 2% | pH is adjusted to 6.8–7.0.

The agar medium thus prepared is inoculated with a cell suspension from an agar slant. The inoculated medium is then incubated at a temperature of 30° C., for a period of 48 hours.

EXAMPLE 2

The following example describes the conditions for a typical isomerization reaction.

After the 48 hour incubation as described in the previous example, cells are removed from the medium and added to 3 ml of potassium phosphate buffer (50 mM, pH 6.5), along with 0.024% $MgSO_4$, and 0.0012% $CoCl_2$. The suspended cells are sonicated for 30 seconds three times to prevent overheating. A 0.5 ml aliquot of the sonicated cell suspension is added to 3.5 ml of potassium phosphate buffer (50 mM, with 0.024% $MgSO_4$, 0.0012% $CoCl_2$, and 5% xylose, pH 6.5) as the substrate for the enzyme. The samples are then incubated at the desired temperature for 5 hours. The isomerization of xylose to xylulose is measured by high pressure chromatography.

EXAMPLE 3

To test the relative level of activity of the isomerization enzyme at very high temperature, the procedure of the preceeding example is followed, with individual samples of the reaction mixtures being incubated at 80° C. and 95° C. for 5 hours. The reaction is terminated by cooling the sample tubes and adding 0.75 ml of 1N HCl.

The isomerization of xylose to xylulose is measured by high pressure liquid chromatography, using the following procedure: the incubated enzyme preparations are centrifuged and the supernatants filtered for injection. The filtered digest is sampled by the automatic WISP sampler in 19 minute intervals. A Waters' carbohydrate column with 20% aqueous acetonitrile mobile phase is employed, using a refraction index detector system combined with automatic peak integration. The amount of product formed at each temperature is determined, and the percentage of product formed at 95° C. vs 80° C. is calculated. The results are discussed in the following example.

EXAMPLE 4

The procedure described in the preceding example is performed using Arthrobacter sp ATCC 21748, and the following known microorganisms: *Bacillus stearothermophilus* B 3682, Ampullariella sp. ATCC 31351, Ampullariella sp. ATCC 31352, Ampullariella sp. ATCC 31353, Ampullariella sp. ATCC 31354, and *Pseudonocardia thermophilia*, ITO No. 12133. The results of the tests comparing the percentage of product obtained at 95° C. vs 80° C. is presented in Table 1. As can be seen from reference to the data, the isomerases of many of the other microorganism lose a significant amount of activity at 95° C. Arthrobacter sp. ATCC 21748, however, retains a proportionately higher level of activity at the higher temperature than any of the other microorganisms tested.

TABLE I

Comparison of the activity of glucose isomerase of various microorganisms under high-temperature conditions.

| Microorganisms | Percent product formed at 95° C. v. 80° C. |
| --- | --- |
| Arthrobacter sp. ATCC 21748 | 55 |
| *Bacillus stearothermophilus* B 3682 | 5 |
| Ampullariella sp. ATCC 31351 | 26 |
| Ampullariella sp. ATCC 31352 | 41 |
| Ampullariella sp. ATCC 31353 | 33 |
| Ampullariella sp. ATCC 31354 | 39 |
| *Pseudonocardia thermophila* | 14 |

TABLE I-continued

Comparison of the activity of glucose isomerase of various microorganisms under high-temperature conditions.

| Microorganisms | Percent product formed at 95° C. v. 80° C. |
| --- | --- |
| ITO No. 12133 | |

What is claimed is:

1. A method of isomerizing glucose to fructose comprising contacting a glucose containing solution, under isomerization conditions, at a temperature between about 90° C. to about 110° C. and a pH within the range of about 6.5 to 7.0, with a thermostable glucose isomerizing enzyme obtained from a biologically pure culture of a strain of microorganism, having the identifying characteristics of Arthrobacter sp. ATCC 21748.

2. The method according to claim 1 wherein said temperature is about 95° C.

3. The method according to claim 1 wherein the pH is about 6.8.

* * * * *